United States Patent [19]
Gergely et al.

[11] Patent Number: 5,415,870
[45] Date of Patent: May 16, 1995

[54] EFFERVESCENT SYSTEMS USING REACTION DOPING AGENTS

[75] Inventors: Gerhard Gergely, Postfach 153, A-1053 Vienna; Thomas Gergely; Irmgard Gergely, both of Vienna, all of Austria

[73] Assignee: Gerhard Gergely, Vienna, Austria

[21] Appl. No.: 170,262

[22] PCT Filed: Jun. 24, 1992

[86] PCT No.: PCT/EP92/01421

§ 371 Date: Dec. 29, 1993

§ 102(e) Date: Dec. 29, 1993

[87] PCT Pub. No.: WO93/00886

PCT Pub. Date: Jan. 21, 1993

[30] Foreign Application Priority Data

Jul. 1, 1991 [CH] Switzerland ............... 1942/91

[51] Int. Cl.$^6$ ............................................. A61K 9/46
[52] U.S. Cl. ................................. 424/466; 424/464
[58] Field of Search .................. 424/466, 464, 475

[56] References Cited

U.S. PATENT DOCUMENTS

| | | | |
|---|---|---|---|
| 2,211,485 | 8/1940 | Zimmermann | 424/466 |
| 3,345,265 | 10/1967 | Grodberg et al. | 424/475 |
| 3,887,700 | 6/1975 | Boncey et al. | 424/44 |
| 4,127,645 | 11/1978 | Witzel et al. | 424/466 |
| 4,678,661 | 7/1987 | Gerggely et al. | 424/44 |
| 4,867,942 | 9/1989 | Gergely et al. | 424/466 |

FOREIGN PATENT DOCUMENTS

| | | |
|---|---|---|
| 374348 | 4/1984 | Austria . |
| 0233853 | 8/1987 | European Pat. Off. . |
| 8800009 | 1/1988 | WIPO . |
| 9107174 | 5/1991 | WIPO . |

OTHER PUBLICATIONS

Database WPIL, Section Ch, Week 8219 Derwent Publications Ltd., London, GB; AN 82-38452E & JP,A,57 056 434 (Kao Soap KK) 5 Apr. 1982.

*Primary Examiner*—Thurman K. Page
*Assistant Examiner*—Sharon Howard
*Attorney, Agent, or Firm*—Ostrolenk, Faber, Gerb & Soffen

[57] ABSTRACT

The effervescent tablet contains an effervescent system composed of carrier crystals of at least one solid, edible, organic acid, at least one component which forms gas by reacting with the acid with salt formation and at least one salt formed from the acid and the gas-forming component. A first layer of a different acid and a second layer of a (preferably acidic) salt of at least one of the two acids are applied to the carrier crystals. Of the total amount of the acid(s) used and of the gas-forming components, 10 to 40, in particular 10 to 20, percent by weight are in the form of the salts, preferably in the form of acidic salts. Carrier crystals are, in particular, citric acid, malic acid, tartaric acid, monosodium citrate and/or ascorbic acid. The first layer may contain gluconic acid delta-lactone and is preferably covered with citric acid, malic acid and/or tartaric acid. This is covered with a layer of a monosalt formed by reaction of part of the total amount of the gas-forming component with at least one of the acids used.

30 Claims, No Drawings

EFFERVESCENT SYSTEMS USING REACTION DOPING AGENTS

The invention relates to an effervescent tablet as can be prepared, for example, by the process according to WO 88/00009. The composition and preparation of effervescent systems known to date are based on a mixture of organic, edible acids with carbon dioxide-forming alkalis and/or alkaline earths which are granulated together or reacted together, dried and compressed with active substances. In this process, all substances are present in more or less powdered or finely crystalline form, and the properties of the resulting product corresponding to the statistical cross-section of the components of the mixture.

In the known effervescent system stated at the outset, the carrier crystal has a reactive core of, for example, citric acid on the inside but monosodium citrate on the outside, as formed ad hoc by individual reaction. The particle thus has the chemical properties of monosodium citrate on the outside; on the inside, however, it still consists of citric acid. Thus, when the first layer of monosodium citrate is dissolved away on contact with water, there is a vigorous reaction with the natural citric acid present within the core.

For various reasons, it is desirable to put pharmaceutical formulations on the market in the form of effervescent tablets: on the one hand, many patients have difficulties in swallowing, particularly in the case of large tablets; on the other hand, many active substances should be taken with at least some water, even if only a modest amount, so that they do not come into contact in concentrated form with the gastric mucus membrane. There have been two problems with effervescent tablets to date: On the one hand, there are many active substances which are themselves moisture-sensitive or react with one of the components of the effervescent system when moisture is present and thus cannot be readily stored, particularly because the citric acid generally used virtually always has a small residual moisture content of 0.2–0.4%. It has therefore been necessary to date to rely in general on very expensive, moisture-resistant packagings.

Even very readily soluble active substances present problems because they rapidly form concentrated solutions when they begin to dissolve in water and thus hinder or slow down the reaction of the effervescent components with one another.

On the other hand, very large effervescent tablets having a total weight of in general 3–4 g have been required to date, particularly for large active substance doses of, for example, 1 g per dose, for achieving acceptable dissolution times, which tablets in turn require large amounts of liquid for dissolution; however, many patients do not readily consume such large amounts of liquid. Moreover, they are expensive with regard to both material required and packaging and may introduce large amounts of undesirable sodium ions into the patient's body. Finally, large effervescent tablets often have a buffer capacity or acid-consuming capacity which is undesirably high for certain applications.

A further difficulty arises from the necessity of using binders in order in the first place to be able to compress the effervescent mixtures to give stable, sufficiently hard tablets. Such binders, such as, for example, sorbitol, polyvinylpyrrolidone, etc., increase the hardness of effervescent tablets but considerably slow down the disintegration and make the tablets additionally moisture-sensitive.

Attempts have already been made to increase the shelf life of sensitive active substances in effervescent tablets by using, for example, anhydrous potassium carbonate (U.S. Pat. No. 3,136,692) as the gas-forming component or monosodium citrate (DE-A1 3920626 or U.S. Pat. No. 4,689,218) as the acidic component; however, such tablets then require a very long time for dissolution because potassium carbonate itself reacts with citric acid much more slowly than, for example, sodium bicarbonate, or the latter reacts much more slowly with monosodium citrate than with citric acid.

For freely soluble active substances, a combination of disintegration agents with the effervescent system has also been proposed (WO 91/07174) because a concentrated active substance solution formed on initial contact of the table with water without disintegration agents hinders the reaction of the effervescent components with one another. This also permits the production of smaller total tablet weights; unfortunately, here too there is the undesirable effect that the solutions become cloudy owing to the disintegration agent.

The WO 88/00009 stated at the outset has already proposed improving the shelf life and reactivity of an effervescent tablet by inducing a slight initial reaction of the acidic and the carbonate components of the effervescent system, resulting—as mentioned—in an effervescent tablet. However, it has been found that the problems just described are only very inadequately solved in this way.

It is therefore the object of the invention to provide an effervescent tablet which has a good shelf life even with pharmaceutically active substances which are moisture-sensitive and/or tend to react with at least one of the components of the effervescent system and/or are freely soluble, and which permits the preparation of smaller effervescent tablets, for example of only 1.5 to 2 gram for up to 1 gram of pharmaceutically active substance, which dissolve in as short a time as possible, the resulting solution being very clear. Finally, the system should also be capable of being readily compressed without the use of dissolution-inhibiting binders and, for certain applications, it should be possible to provide effervescent tablets having a very low acid-consuming capacity.

These objects are satisfactorily achieved in a surprising manner, according to the invention, by the measures described below.

The present invention relates to the preparation of effervescent particles having an individual structure, where the internal and external properties of the effervescent particles can be quasi-programmed by means of various novel measures.

The basic requirement for this novel technology is the use of carrier crystals of edible, organic acids because these crystallize in regular form, are available in suitable crystal sizes and, owing to their physical properties, are particularly suitable for doping. The more freely soluble an acid, the more readily can the crystals be wet and subsequently covered or passivated. However, the acid must in each case be present in excess and in suitable particle size so that actually only the surface is wet and the formation of any pasty mass, which could not be further processed according to the invention, is avoided.

Carbonates and bicarbonates are not suitable carrier crystals because they cannot be doped; they repel water.

The simplest case is when defined citric acid crystals, having a crystal size of 0.1 to 0.6 mm, in particular 0.2 to 0.4 mm, are wet with water or with a buffer solution (WO 88/00009) or with a concentrated gluconic acid delta-lactone solution (U.S. Pat. No. 4,678,661, Example 4) and allowed to react with alkaline earth metal carbonates, and this reaction is stopped at a certain time. This gives individual effervescent particles which are already relatively resistant to moisture but are not suitable for all active substances or for all possible variations. If in fact the reaction is continued too far, i.e. if, for example, more than 5 or 10% of the acid surface is converted into alkali metal salts, the effervescent system becomes too slow.

Example 4 of the stated U.S. Pat. No. 4,678,661 relates to a different object (it is intended to prepare a low-sodium effervescent tablet—and not a particularly small one), to a different technical measure for achieving this object (the first layer of a gas-forming component applied always comprises calcium carbonate which is absent in the present invention) and to a different result (standard effervescent tablets of 3.5 or 4 g—and not of about 2 gram or even less, according to the invention—are prepared).

According to the invention, it has now been found that the system can be accelerated in the reaction if foreign acids are simultaneously incorporated in the surface. Thus, for example, alkali metal salts of a plurality of acids are formed in a plurality of layers, preferably 10 to 40% of the effervescent system reacting to form the salt—in particular only the monosalt.

Finally, owing to the possibility of preparing small effervescent tablets, the invention also makes it possible to keep the content of sodium ions low and to prepare effervescent tablets having only a very low acid-consuming capacity of, for example, $\leq 5$ meq.

Thus, malic acid, tartaric acid or gluconic acid delta-lactone can be incorporated, for example, into a citric acid crystal surface, preferably heated to temperatures between 50° and 60° C., by means of, in particular, very concentrated, aqueous, alcoholic or aqueous alcoholic solutions, and this crystal surface doped with foreign acids can then be allowed to react with alkali metal carbonates and/or alkali metal bicarbonates and optionally—in particular in the case of gluconic acid delta-lactone—with further acids having a different pK value.

The way in which these systems are prepared, whether, for example, malic acid and citric acid—both as carrier crystals—are used and either a citric acid solution or gluconic acid delta-lactone solution is then applied and the bicarbonate is then allowed to react, depends on the physical and chemical properties of the active substances to be processed. However, the doping with a foreign acid or with the gluconic acid delta-lactone and the conversion to the monosalt always remain. The ratios of the acids to one another are usually, for example in the case of citric acid to malic acid, about 8:1 but may also be 3:1.

Such systems dissolve substantially more rapidly because, owing to the different pH and pK values of the two or more acids, the formation of a reaction-retarding buffer solution during the dissolution is continuously disturbed locally and thus prevented. In the case of the effervescent particles according to the invention, the lattice defect which causes this is already present and does not have to form, as would be the case, for example, with mixtures of two different acids, occasionally used in the past.

For example, an equilibrium pK of 3.14 is established at the boundary layer of a citric acid crystal; if, however, another acid having a higher or lower pK is present there in the lattice, the equilibrium is disturbed; no stable buffer forms, and the individual particles—and hence the tablet—dissolve more rapidly. However, both acids must have partially reacted; if this is the case for only one acid, then the tablet may not have a sufficiently long shelf life.

In the case of a tribasic, moderately weak acid, the pH depends on the pK according to a fourth degree equation; in this case, different pH values or buffers form at various points.

The system can be further changed if, for example, it is desired to incorporate active substances which are sensitive to alkalis. In this case, the alkaline surface formed by reaction of the carrier crystal with alkali metal or alkaline earth metal carbonates can be further acidified by applying, in a further step, acid solutions or at least powdered acid, in particular the slightly soluble fumaric acid. In this case too, an intermediate layer of gluconic acid delta-lactone may improve coherent layer formation of the acid.

Since carrier systems prepared in this manner are as such extremely stable, they are also very moisture-insensitive because the acid surface is quasi-passivated; they do not react with atmospheric humidity but react only when water is present.

While systems of the prior art begin to react substantially with effervescence at 90% atmospheric humidity after only 5 to 10 minutes, systems having the composition according to the invention are stable for up to 10 hours at 90% atmospheric humidity, without exhibiting bubbles or reaction.

The gluconic acid delta-lactone is particularly readily soluble (1 part of gluconic acid delta-lactone in 0.5 part of water), especially at relatively high temperatures. This lactone is hydrolysed by water to form gluconic acid, probably particularly when it comes into contact with alkalis in aqueous solution. It also acts as a neutral granulating aid for precoated carrier crystals, for example when mixed with sodium carbonate; in contact with water, in particular in the presence of alkalis, it is converted into reactive gluconic acid.

If the reaction of the components of the effervescent system is now continued in the above-mentioned manner (particularly when the salt being formed, for example monosodium citrate, is produced in anhydrous form, as occurs, for example, when the reaction takes place in vacuo), the passivation results in a long shelf life, not only owing to the masking of the citric acid but also due to the "internal" moisture consuming capacity of the resulting anhydrous salt.

In the process according to the invention, alkali metal carbonates or alkali metal bicarbonates are allowed to react on the surface of the carrier particles to a considerable extent, preferably to an order of magnitude of 10 to 40%. In the preparation of the effervescent base, a reaction loss of 5 to 10%, but not more than 15%, may be expected, the resulting $CO_2$ and water being removed by means of a vacuum. This reaction loss of 5 or 10% of the total amount of citric acid, bicarbonate and carbonate used means that, at a reaction loss of 5%, 16.8% and, at a reaction loss of 10%, 33.5% of the total amount of effervescent components used are present as monocitrate. In fact, this would in general lead to slowly dissolving effervescent tablets, since the sodium salt formed as a result acts as a buffer system and slows down the dissolution, but not when, according to the invention, foreign acids have been incorporated.

If, for example, a concentrated solution of 100 parts by weight of malic acid is applied to 900 parts by weight of a citric acid carrier, preferably to citric acid crystals having a particle size of 0.1 to 0.6 mm, and this malic acid solution is allowed to penetrate into the surface of the citric acid at elevated temperatures, for example at 60° C., and if 10 to 20 parts by weight of sodium bicarbonate powder are then applied to this surface and are allowed to react until gas evolution ceases, then the remaining amount of sodium bicarbonate, for example 400 parts by weight, can furthermore be allowed to undergo partial reaction with still moist and accordingly tacky material and can be dried.

If this system is compressed to give tablets, hardnesses of 12 to 20 kp are obtained at a tablet diameter of 18 to 20 mm, the dissolution rate being about 30 to 40 seconds.

The achievable unusual hardnesses have a physical explanation: the crystal lattice of the carrier acid is disturbed at the surface by the applied concentrated second acid, a surface melting point depression resulting. This crystal defect is further increased if alkali metal ions are introduced into this surface mixture by reaction. It has been found that carrier acid crystals treated in this manner at the surface have extremely high binding forces on compression of the tablets, said forces also making it possible to compress active substances which are difficult to press and to achieve sufficient tablet hardnesses even without further binders. In such a system, it is therefore possible to dispense with every binder. On the other hand, this system nevertheless permits the use of pharmaceutical fillers or excipients, such as, for example, sucrose, sorbitol, mannitol or the like, if they are desired for certain reasons, for example also for reducing the moisture sensitivity of the effervescent tablets, without substantially increasing the dissolution times of the tablets as a result. Finally, the inert filler prevents the generally undesired interaction of the active substance with reactive components of the effervescent system.

The rapid dissolution of such systems arises for two reasons:

1.) The alkali metal bicarbonate or carbonate particles are closely associated with the reacted surface of the acid crystals, so that, after drying, a transition layer from pure acid crystals through the reaction layer to the pure alkali metal carbonate or bicarbonate forms. If such a system enters water, the formation of a buffer system will occur in the case of the presence of particularly large particles of an acid in the binding layer alone,, said buffer system retarding the further reaction between inner and outer layers. In many commercial effervescent tablets, it is possible to observe that, after the initial dissolution of the tablet, a core remains which now reacts further only very slowly. This is because the resulting salt solution, for example sodium citrate solution, acts as a buffer between the particles of the effervescent tablet and hinders their further reaction.

2.) The resulting buffer solution is always disturbed by virtue of the fact that carrier particles of different sizes dissolve at different rates and/or different acids having different pH or pK values hinder the formation of a static buffer. The pH in the boundary layers is continuously changed and disturbed since two or more acids having different pK values influence one another.

The system can be further improved if, after moistening by means of, for example, malic acid solution, the citric acid is additionally covered with a powdered third acid, preferably with at least one less moisture-sensitive compound, such as, for example, tartaric acid, fumaric acid or adipic acid. This structure, too, is then allowed partially to react with alkali metal carbonates or alkali metal bicarbonates, sodium citrates, sodium maleates, etc. forming in the interior of the system, while sodium fumarate, sodium adipate or sodium tartrate, which are generally very particularly insensitive to atmospheric humidity, form on the outer shell of the particle. These systems, too, exhibit rapid disintegration after a short time in water and are therefore extremely suitable for mixing with various active substances.

It is true that in principle any solid, edible, organic acid can be used as a carrier crystal. However, citric acid is preferred; to use predominantly tartaric acid would be too expensive; malic acid alone as carrier crystals requires cooling of the granules before further processing, which means an additional step in production.

This structure consisting of two or three edible acids is then caused to undergo a partial reaction with alkali metal carbonates and then covered with further amounts of alkali metal carbonate and/or alkali metal bicarbonates. In this procedure, only some of the sodium bicarbonate, for example, is added and is reacted to give monosodium citrate until no further gas is evolved. Only then is the remaining sodium bicarbonate and/or potassium bicarbonate added and bound to the surface by partial reaction (partial conversion into the monocitrate or monomaleate or monotartrate). This results in a very wide range of alkali metal salts of two or three different organic acids, accounting for 5 to 15% of the total effervescent system.

Although it is not essential to apply the bicarbonate in two parts, this facilitates the process since, by using a certain amount of sodium bicarbonate which is allowed to react completely to form monosodium citrate, the reaction can be more easily controlled and can be allowed to take place in a more defined manner than is possible with the use of the total amount of the alkalis by means of a partial reaction only. The amount of the alkali metal bicarbonate or carbonate reacted with acid is between 2 and 20%, calculated in relation to the total amount of the alkalis used. On average, 5 to 10% of the alkalis used are reacted in a first step. In contrast, only 2% of the alkalis used are reacted in the first step in the subsequent Example 8 (paracetamol), owing to the fact that a very large amount of sodium bicarbonate is used here, whereas almost 20% are reacted in the subsequent Example 5 (minoxidil). This is due to the active substance on the one hand and to the pH on the other. However, it is also entirely possible to double the amount of bicarbonate in the first step in the paracetamol example.

More alkalis than are required for the formation of the monosalt are preferably present, especially in those cases where the pH is to be above that of monosodium citrate, which is 3.9 to 4.15; in solution, effervescent tablets should have a pH of 4.3 to 4.5 or even more.

Finally, in the case of alkali-sensitive active substances, the granules may furthermore be moistened by means of a gluconic acid delta-lactone solution and then covered with either citric acid or fumaric acid in order to obtain an acidic layer on the outside. In other cases, granulation is finally effected with gluconic acid delta-lactone and anhydrous sodium carbonate. In the case of substances which are not alkali-sensitive, the latter step, the addition of gluconic acid delta-lactone solution and the final covering with citric acid, can be omitted.

The Examples which follow relate to three systems which differ fundamentally from one another. Either the active substance is alkali-sensitive and the sodium bicarbonate must be very firmly bound to the citric acid by partial reaction (these include acetylcysteine, captopril (where the base is additionally covered with citric acid) and minoxidil) or the active substances are especially moisture-sensitive (these include ambroxol, ranitidine and cimetidine). Active substances which have to be present in a small tablet in very large amounts are sucralfate, ascorbic acid, arginine aspartate and mesna.

Effervescent systems for arginine aspartate and sucralfate, which are neutral substances, do of course have a slightly different composition compared with paracetamol, which is alkaline. Aspirin, which has an acidic pH, is in contrast to this.

Particularly with the use of vacuum mixing or granulating drums, the process according to the invention makes it possible exactly to tailor or even to preprogram effervescent systems to the particular active substance and its amount and optionally even to allow the individual steps to take place under computer control.

Example 1 (Acetylcysteine)

200 mg of the active substance acetylcysteine are included in a 1.3 g tablet. The acetylcysteine is sensitive to alkalis and is converted by alkaline oxidation (interaction with, for example, sodium bicarbonate; it is relatively stable to sodium carbonate) into the unstable dimer. In order to prevent this, the sodium bicarbonate is very strongly bound to the citric acid by reaction and partial conversion into sodium citrate, in order to ensure that free sodium bicarbonate, which may interact with the acidic acetylcysteine, is present in as small amount as possible.

| Parts: | |
|---|---|
| 379 | Crystallized citric acid |
| 100 | Malic acid |
| 105 | Citric acid powder |
| 20 | Sodium bicarbonate I |
| 180 | Sodium bicarbonate II |
| 100 | Sodium carbonate |
| 6 | Gluconic acid delta-lactone for solution |
| 890 | |
| 200 | Acetycysteine |
| 156 | Additives |
| 1246 | |

Process: Heat citric acid and malic acid to 60° C. and moisten with 6 ml of a gluconic acid delta-lactone solution (10 parts of gluconic acid delta-lactone, 5 parts of water). Add sodium bicarbonate I and allow reaction to give monosodium citrate; then allow sodium bicarbonate II to undergo partial reaction (partial conversion to the citrate). Add citric acid powder and cover the surface by partial reaction. Add sodium carbonate and allow to undergo partial reaction and finally dry in vacuo. This effervescent base is mixed with 200 parts of acetylcysteine and with corresponding fillers, aromas and sweeteners.

Example 2 (Acetylcysteine)

| Parts | |
|---|---|
| 275 | Crystallized citric acid |
| 45 | Tartaric acid |
| 75 | Citric acid powder |
| 20 | Sodium bicarbonate I |
| 240 | Sodium bicarbonate II |
| 138 | Sodium carbonate |
| 12 | Monosodium citrate in 30% aqueous solution |
| 805 | |
| 600 | Acetylcysteine |
| 215 | Additives |
| 1620 | |

Process: Heat crystallized citric acid and tartaric acid to 50° C.; allow monosodium citrate solution to penetrate, and cover with citric acid powder; then add sodium bicarbonate I and react to give monosodium citrate; then add the remaining sodium bicarbonate and allow partial reaction (partial conversion to the citrate); finally add sodium carbonate and allow partial reaction. 600 parts of acetylcysteine and additives, aromas and sweeteners are added to these base granules.

Example 3 (Ambroxol)

The heat-sensitive and moisture-sensitive ambroxol is bound by means of malic acid solution to a highly passivated and hence insensitive base comprising carrier crystals of citric acid and tartaric acid.

| Parts | |
|---|---|
| 515 | Crystallized citric acid |
| 170 | Tartaric acid |
| 25 | Sodium bicarbonate I |
| 325 | Sodium bicarbonate II |
| 60 | Sodium carbonate |
| 6 | Malic acid for solution I |
| 1101 | |
| 30 | Ambroxol HCl |
| 244 | Additives to |
| 1375 | |

Process: Heat crystallized citric acid and tartaric acid to 60° C. and moisten with 8 ml of 60% malic acid solution. Allow sodium bicarbonate I to react until monosodium citrate is formed, and then allow sodium bicarbonate II to undergo partial reaction (partial conversion to citrate). Add sodium carbonate, allow to undergo partial reaction and dry in vacuo. Mix the resulting granules with ambroxol HCl and the additives (sweetener, aroma) and compress to give tablets.

Example 4 (Captopril)

Owing to its chemical structure, captopril is even more highly sensitive than acetylcysteine to alkaline substances, under the influence of which it forms the unstable dimer. Here, binding the bicarbonates to the citric acid is not in itself sufficient, and the effervescent base must also be passivated by a layer of powdered citric acid or by means of citric acid solution or gluconic acid delta-lactone solution.

| Parts | |
|---|---|
| 250 | Crystallized citric acid |
| 55 | Monosodium citrate |
| 67 | Malic acid |
| 63 | Fumaric acid |
| 11 | Sodium bicarbonate I |
| 173 | Calcium carbonate |
| 36 | Sodium carbonate |
| 10 | Gluconic acid delta-lactone |
| 665 | |
| 25 | Captopril |
| 110 | Additives |
| 800 | |

Process: Heat crystallized citric acid, monosodium citrate and malic acid to 60° C. Moisten with 10 ml of gluconic acid delta-lactone solution (10 parts of gluconic acid delta-lactone, 5 parts of water). Add sodium bicarbonate I and allow to reaction until monosodium citrate forms; then add sodium carbonate and calcium carbonate and allow to react; then add fumaric acid powder and cover the surface by partial reaction; then dry in vacuo. This base is mixed with 25 parts of captopril and the additives, such as, for example, sweeteners, aromas and any fillers.

Example 5 (Minoxidil)

| Parts | |
|---|---|
| 243 | Crystallized citric acid |
| 80 | Malic acid |
| 120 | Citric acid powder |
| 39 | Sodium bicarbonate I |
| 61 | Sodium bicarbonate II |
| 79 | Potassium bicarbonate |
| 70 | Sodium carbonate |
| 10 | Gluconic acid delta-lactone for solution |
| 702 | |
| 10 | Minoxidil |
| 38 | Additives |
| 750 | |

Process: Heat crystallized citric acid and malic acid to 60° C. and moisten with 10 ml of gluconic acid delta-lactone solution (10 parts of gluconic acid delta-lactone to 5 parts of water); add sodium bicarbonate I and allow reaction until monosodium citrate forms. Then add sodium bicarbonate II and potassium bicarbonate and allow partial reaction (partial conversion to the citrate). Then add citric acid powder and cover the surface by partial reaction. Finally add sodium carbonate and allow partial reaction and finally dry in vacuo. This effervescent base is mixed with 10 parts of minoxidil and with the additives (for example, sweeteners and aroma).

Example 6 (Ranitidine)

| Parts | |
|---|---|
| 630 | Crystallized citric acid |
| 210 | Tartaric acid |
| 210 | Citric acid powder |
| 370 | Monosodium citrate |
| 40 | Sodium bicarbonate I |
| 460 | Sodium bicarbonate II |
| 100 | Sodium carbonate |
| 16 | Gluconic acid delta-lactone for solution |
| 2036 | |
| 170 | Ranitidine HCl |
| 294 | Additives |
| 2500 | |

Process: Heat crystallized citric acid, tartaric acid and monosodium citrate to 60° C. Moisten with 16 ml of a gluconic acid delta-lactone solution (10 parts of gluconic acid delta-lactone, 5 parts of water). Add sodium bicarbonate I, which is converted completely into monosodium citrate.

Then allow sodium bicarbonate II to undergo partial reaction (partial conversion to the citrate). Add citric acid powder and cover the surface by partial reaction. Finally allow sodium carbonate to undergo partial reaction and dry in vacuo. This effervescent base is mixed with 170 parts of ranitidine HCl and corresponding additives, such as sweetener and aroma.

Example 7 (Cimetidine)

200 mg of active substance are included in a 2.3 g tablet:

| Parts | |
|---|---|
| 706 | Crystallized citric acid |
| 200 | Malic acid |
| 250 | Citric acid powder |
| 16 | Sodium bicarbonate I |
| 462 | Sodium bicarbonate II |
| 102 | Sodium carbonate |
| 6 | Citric acid in 50% aqueous solution |
| 1742 | |
| 200 | Cimetidine |
| 368 | Additives |
| 2310 | |

Process: Heat crystallized citric acid and malic acid to 60° C., moisten with 6 ml of 50% citric acid solution, add sodium bicarbonate I and allow reaction to give monosodium citrate. Then allow sodium bicarbonate II to undergo partial reaction (partial conversion to the citrate). Cover the surface by partial reaction with citric acid powder; finally allow sodium carbonate to undergo partial reaction and dry in vacuo. This effervescent base is mixed with 200 parts of cimetidine and corresponding additives (fillers, aromas and sweeteners).

Example 8 (Paracetamol)

500 mg of paracetamol can be incorporated, according to the invention, in a 2.74 g tablet with good dissolution properties.

The problem in the case of the paracetamol effervescent tablet is that the paracetamol is alkaline and the preferred DH of the ready-to-drink solution is about 6, so that an excess of alkaline substance, such as bicarbonate or carbonate, prevents rapid dissolution, since a relatively small amount of citric acid is present and hence the formation of an active substance core which is poorly soluble is promoted. By means of the novel granulating principle, it is possible to overcome these disadvantages.

| Variant I | | Variant II | |
|---|---|---|---|
| Parts | | Parts | |
| 765 | Crystallized citric acid | 415 | Malic acid |
| 150 | Malic acid | 500 | Crystallized citric acid |
| 20 | Sodium bicarbonate I | 20 | Sodium bicarbonate I |
| 913 | Sodium bicarbonate II | 913 | Sodium bicarbonate II |
| 150 | Sodium carbonate | 150 | Sodium carbonate |
| 25 | Gluconic acid delta-lactone for solution I | 25 | GDL for solution I |
| 2023 | | 2023 | |
| 500 | Paracetamol | 500 | Paracetamol |
| 50 | Gluconic acid delta-lactone for solution II | 50 | GDL for solution II |
| 167 | Additives | 167 | Additives |
| 2740 | | 2740 | |

Process: Heat crystallized citric acid and malic acid to 50° C. and moisten with 25 ml of gluconic acid delta-lactone solution (10 parts of gluconic acid delta-lactone to 5 parts of water) (the citric acid is doped); allow sodium bicarbonate I to react to give monosodium citrate; then allow sodium bicarbonate II to undergo partial reaction (partial conversion to the citrate); then allow sodium carbonate to undergo slight partial reaction. Then add paracetamol. Granulate with 50 ml of gluconic acid delta-lactone solution (10 parts of gluconic acid delta-lactone to 5 parts of water). Then dry in vacuo. Mix the base granules obtained with corresponding additives, such as sweeteners and aromas.

Example 9 (Acetylsalicylic acid)

A 2.6 g tablet contains 500 mg of acetylsalicylic acid and, in order to achieve a reduced sodium content, also potassium salts and calcium salts as alkalis. Since the acidic aspirin tends to interact with the alkali metal carbonates, the base was covered with citric acid.

| Parts | |
|---|---|
| 259 | Crystallized citric acid |
| 130 | Crystallized malic acid |
| 264 | Citric acid powder |
| 15 | Sodium bicarbonate I |
| 466 | Sodium bicarbonate II |
| 46 | Calcium carbonate |
| 137 | Potassium bicarbonate |
| 132 | Potassium carbonate |
| 42 | Sodium carbonate |
| 27 | Gluconic acid delta-lactone for solution |
| 1518 | |
| 500 | Aspirin |
| 47 | Additives |
| 2065 | |

Process: Apply crystallized citric acid, then heat to 60° C. and wet with 36 ml of gluconic acid delta-lactone solution (10 parts of gluconic acid delta-lactone to 5 parts of water); apply malic acid, then allow sodium bicarbonate I to react to give monosodium citrate and malate and then allow sodium bicarbonate II, calcium carbonate and potassium bicarbonate to undergo partial reaction (partial conversion to the citrate). Then cover the surface with citric acid powder. Finally allow sodium carbonate to undergo partial reaction, and dry in vacuo. This effervescent base is mixed with 500 parts of aspirin and with corresponding additives.

Example 10 (Arginine aspartate)

Arginine aspartate is particularly freely soluble and, in conventional effervescent systems, by the formation of concentrated solutions, prevents the rapid effervescence of the tablet.

| Parts | |
|---|---|
| 384 | Crystallized citric acid |
| 53 | Sodium bicarbonate I |
| 144 | Sodium bicarbonate II |
| 88 | Potassium bicarbonate |
| 61 | Sodium carbonate |
| 6 | Malic acid for solution I |
| 736 | |
| 1000 | Arginine aspartate |
| 41 | Additives |
| 1777 | |

Process: Heat citric acid to 60° C. and moisten with 8 ml of 60% malic acid solution. Allow sodium bicarbonate I to react to give monosodium citrate and malate; then allow sodium bicarbonate II and potassium bicarbonate to undergo partial reaction. Add sodium carbonate and allow partial reaction, and then dry in vacuo. Mix the resulting granules with arginine aspartate and the additives (Sweetener, aroma) and compress to give tablets.

Example 11 (Sucralfate)

In the preparation of a sucralfate tablet, a very small amount of sodium bicarbonate is available. It must therefore be granulated together with the second bicarbonate by means of gluconic acid delta-lactone solution.

| Parts | |
|---|---|
| 394 | Crystallized citric acid |
| 42 | Sodium bicarbonate I |
| 158 | Sodium bicarbonate II |
| 6 | Malic acid for solution |
| 200 | Gluconic acid delta-lactone for solution |
| 800 | |
| 1000 | Sucralfate |
| 100 | Additives |
| 1900 | |

Process: Heat crystallized citric acid to 60° C. and wet with 8 ml of 60% malic acid solution. Allow sodium bicarbonate I to react to give monosodium citrate, add sucralfate and sodium bicarbonate II and granulate with 280 ml of gluconic acid delta-lactone solution (10 parts of gluconic acid delta-lactone/3 parts of water/3 parts of ethanol) and then dry in vacuo. Mix the granules with the additives (sweetener, aroma).

Example 12 (Mesna)

| Parts | |
|---|---|
| 610 | Crystallized citric acid |
| 40 | Tartaric acid |
| 34 | Sodium bicarbonate I |
| 236 | Sodium bicarbonate II |
| 68 | Sodium carbonate |
| 12 | Malic acid for solution I |
| 1000 | |
| 1000 | Mesna |

-continued

Examples 1 to 13 are clearly summarized in the Table below. The meanings are as follows:

| Example | Carrier crystals | Layer on the carrier crystals | | | | | 6 Active substance | 7 |
|---|---|---|---|---|---|---|---|---|
| | | 1 | 2 | 3 | 4 | 5 | | |
| 1 | CA, MA | GDL | BC1 | BC2 | CA | SC | Acetylcysteine | |
| 2 | CA, TA | MNC | CA | BC1 | BC2 | SC | Acetylcysteine | |
| 3 | CA, TA | MA | BC1 | BC2 | SC | | Ambroxol | |
| 4 | CA, MNC, MA | GDL | BC | CC | FA | SC | Captopril | |
| 5 | CA, MA | GDL | BC1 | BC2 KH | CA | SC | Minoxidil | |
| 6 | CA, TA, MNC | GDL | BC1 | BC2 | CA | SC | Ranitidine | |
| 7 | CA, MA | CA | BC1 | BC2 | CA | SC | Cimetidine | |
| 8 | CA, MA | GDL | BC1 | BC2 | SC | | Paracetamol | GDL |
| 9 | CA | GDL | MA | BC1 | BC2 CC, KH | CA SC | Acetylsalicylic acid | |
| 10 | CA | MA | BC1 | BC2 | KH | SC | Arginine aspartate | |
| 11 | CA, MA | BC1 | BC2 | GDL | | | Sucralfate | |
| 12 | CA, MA | TA | BC1 | BC2 | SC | | Mesna | |
| 13 | CA Vit. C, MA | BC1 | BC2 | SC | | | | |

CA Citric acid (in carrier crystals as fine particles, in the layers as powder)
MA Malic acid
FA Fumaric acid
TA Tartaric acid
CC Calcium carbonate
SC Sodium carbonate
KH Potassium bicarbonate
MNC Monosodium citrate
GDL Gluconic acid delta-lactone (67% solution)
BC1 Sodium bicarbonate, 1st part (reacted to give the monosalt)
BC2 Sodium bicarbonate, 2nd part (anchored to the preceding layers only by partial reaction)

| Parts | |
|---|---|
| 78 | Additives |
| 2078 | |

Process: Heat crystallized citric acid to 60° C., wet with 14 ml of 70% malic acid solution, apply tartaric acid and allow to penetrate. Allow sodium bicarbonate I to react to give monosodium citrate and malate; add sodium bicarbonate II and allow partial reaction (partial conversion to the citrate). Add sodium carbonate and dry in vacuo. Mesna is granulated with a 30% sorbitol solution in 1:1 alcohol/water, dried, sieved and mixed with the effervescent base prepared according to the Example and with any desired additives and compressed to give tablets.

Example 13 (Vitamin C)

| Parts | |
|---|---|
| 1020 | Ascorbic acid |
| 588 | Crystallized citric acid |
| 50 | Sodium bicarbonate I |
| 350 | Sodium bicarbonate II |
| 140 | Sodium carbonate |
| 12 | Malic acid for solution |
| 2160 | |
| 40 | Additives |
| 2200 | |

Process: Heat crystallized citric acid and ascorbic acid to 60° C. Moisten with 16 ml of 60% malic acid solution. Allow sodium bicarbonate I to react to give monosodium citrate and malate; then allow sodium bicarbonate II to undergo partial reaction. Add sodium carbonate and allow to undergo partial reaction. Then dry in vacuo. Mix the resulting granules with the additives (sweetener, aroma).

Except in Examples 8, 11 and 13, the active substance is mixed with the prepared effervescent base and compressed to give tablets. In Examples 8 and 11, the active substance is mixed with one or more other layer component(s) and applied as a layer; in Example 13, the active substance (vitamin C=ascorbic acid) is taken with citric acid as the carrier crystal.

Example 14 (Arginine aspartate and acetylcysteine)

A Table showing the variation of the different effervescent bases appears below. The following five effervescent bases were prepared by the principle according to the invention:

| Effervescent base | a | b | c | d | e |
|---|---|---|---|---|---|
| Citric acid, fine particles | 900 | | | | 900 |
| Citric acid for solution | | 19 | 19 | 19 | 24 |
| Tartaric acid type 2V | | 900 | 100 | | |
| Tartaric acid powder | 100 | | | | |
| NaHCO₃ (BC1) | 50 | 50 | 50 | 50 | |
| NaHCO₃ (BC2) | 350 | 350 | 350 | 350 | |
| Na₂CO₃ | 100 | 100 | 120 | 270 | 100 |
| Malic acid, fine particles | | 100 | 900 | 900 | |
| Malic acid for solution | 19 | | | | |
| Adipic acid | | | | 100 | |
| Fumaric acid | | | | | 100 |
| KHCO₃ | | | | | 150 |
| K₂CO₃ | | | | | 250 |

These five effervescent bases a to e were each mixed in alternating amounts with 1000 mg of arginine aspartate or with 1000 mg of acetylcysteine and 290 mg of Na₂CO₃ and compressed to give tablets. The resulting tablet hardnesses, dissolution times in only 50 ml of water and pH achieved are shown:

| Effervescent base | 1000 mg of arginine aspartate | | 1000 mg of cysteine | | acetyl- |
| --- | --- | --- | --- | --- | --- |
| | 500 mg | 750 mg | 1000 mg | 460 mg | 710 mg |
| a | | | | | |
| Hardness | 5.9 | 6.3 | 6.5 | 6–7 | 6–7 |
| Dissolution time | 50" | 50" | 60" | 70" | 75" |
| pH | 4.5 | 4.45 | 4.35 | 4.3 | 4.4 |
| b | | | | | |
| Hardness | 6.1 | 5.9 | 7.6 | 7.1 | 7.5 |
| Dissolution time | 50" | 70" | 100" | 100" | 115" |
| pH | 4.3 | 4.1 | 4.1 | 4.01 | 4.1 |
| c | | | | | |
| Hardness | 6.0 | 6.2 | 7.2 | 6–7 | 6–7 |
| Dissolution time | 50" | 50" | 75" | 90" | 80" |
| pH | 4.5 | 4.4 | 4.3 | 4.1 | 4.3 |
| d | | | | | |
| Hardness | 5.9 | 7.2 | 6.2 | 6–7 | 6–7 |
| Dissolution time | 60" | 80" | 70" | 75" | 85" |
| pH | 4.99 | 4.86 | 4.9 | 5.1 | 5.1 |
| e | | | | | |
| Hardness | 5.9 | 6.9 | 6.2 | 6–7 | 6–7 |
| Dissolution time | 80" | 75" | 60" | 50" | 60" |
| pH | 4.55 | 4.5 | 4.39 | 4.4 | 4.35 |

Example 15

Dimethicone (dimethylpolysiloxane) is usually used as an antifoam for suspensions, for example during tablet coating, or in some cases also for creams and effervescent tablet formulae. Dimethicone has also been used to date to reduce the moisture sensitivity of effervescent tablets. According to the invention, however, it is now possible to increase the reaction rate of the effervescent tablet by 20 to 30%, i.e. accelerate the dissolution, by adding dimethicone applied to a carrier in small amounts. The dimethicone evidently results in an improvement in the contact between the effervescent reactants during the reaction, this being achieved by applying small amounts of dimethicone to a neutral carrier and mixing the latter with the effervescent base.

The procedure is as follows: 100 parts by weight of neutral fillers, such as, for example, mannitol, sorbitol, lactose, maltodextrin or Aerosil, are heated to 40° C. A solution of 0.1 to 0.8 parts by weight of dimethicone in organic solvents is sucked into a vacuum drum containing this carrier. The solvent is evaporated during thorough stirring, in order to obtain an appropriate uniform distribution. The product thus obtained is added to the effervescent tablet in an amount between 0.1 and 0.6 mg per tablet, depending on the active substance, whose hydrophobic or hydrophilic character also plays a role here. For example, a dissolution time of 80 sec is achieved for a cimetidine effervescent tablet without dimethicone whereas a dissolution time of 55 sec is achieved with the same hardness in the presence of dimethicone.

In the case of ambroxol, the dissolution time can be decreased from 120 sec to 70–80 sec by adding 100 mg of mannitol to which 0.4 mg of dimethicone has been applied.

We claim:

1. An effervescent tablet containing at least one pharmaceutically active substance and an effervescent system comprising at least one solid, edible, organic acid, at least one alkali metal carbonate or bicarbonate as a gas-forming component and at least one alkali metal salt of the acid, wherein there are at least two layers applied to carrier crystals consisting of the said at least one acid, wherein the first layer contains at least one solid, edible, organic acid different from said crystal acid or the alkali metal salt of said different acid, or both, whereas the second layer contains at least one alkali metal salt of said at least one acid.

2. An effervescent tablet as claimed in claim 1, wherein, of the total amount of the acids used and of the gas-forming components, 10 to 40, percent by weight are present in the form of the salts.

3. An effervescent tablet as claimed in claim 1, adapted especially for an especially moisture-sensitive active substance, wherein at least a part of the salt of the gas-forming component is or both is present in essentially anhydrous form.

4. An effervescent tablet as claimed in claim 1, wherein the effervescent system has an acid-consuming capacity of not more than 5 meq.

5. An effervescent tablet as claimed in claim 1, which contains 0.1 to 0.6 mg of dimethicone, applied to a neutral excipient or carrier.

6. An effervescent tablet as claimed in claim 1, which contains fifteen to thirty parts by weight of fillers or excipients, per 100 parts by weight of the effervescent system.

7. An effervescent tablet as claimed in claim 1, which contains at least two edible organic acids having different pK values.

8. An effervescent tablet as claimed in claim 1, wherein the gas-forming components are present in a substoichiometric amount.

9. An effervescent tablet as claimed in claim 1, wherein about 5 to about 20, percent by weight of the total amount of gas-forming components have reacted to give the monosalt and are present in this form in a second or third layer, while the remainder in the layer above this is anchored to the carrier crystal only by partial reaction.

10. An effervescent tablet as claimed in claim 1, wherein, in the sequence citric acid-malic acid-tartaric acid-adipic acid, a first acid is present in the carrier particle, on whose surface at least one subsequent acid or its salt is anchored and is at least partly covered with at least a part of the gas-forming component with formation of an intermediate layer consisting of the salt.

11. An effervescent tablet as claimed in claim 1, wherein a mixture of citric acid with at least one of the following compounds is present as carrier crystals: malic acid, tartaric acid, and monosodium citrate.

12. An effervescent tablet as claimed in claim 1, wherein the first layer contains malic acid, unless the carrier crystals consist exclusively of malic acid.

13. An effervescent tablet as claimed in claim 1, having a first layer of gluconic acid delta-lactone, wherein the first layer is covered with at least one of the following acids or alkali metal salts thereof: citric acid, malic acid, and tartaric acid.

14. An effervescent tablet as claimed in claim 1, wherein the second layer is formed from a proportion of the total amount of the gas-forming component, at least partially in the form of the monosalt of the acid forming the carrier crystals or the first layer or both.

15. An effervescent tablet as claimed in claim 1, having an alkali-sensitive substance, wherein the layer applied to the carrier crystals is covered with the gas-forming components by means of an acid.

16. An effervescent tablet as claimed in preceding claim 1, which contains—based on 100 parts by weight of the effervescent system—at least 50, parts by weight of the pharmaceutically active substance, and wherein the carrier crystals coated in this manner are present as a mixture with gluconic acid delta-lactone or sodium carbonate, or both the mixture being in the form of granules.

17. A process for the preparation of an effervescent system comprising at least one solid, edible, organic acid, at least one component which forms a gas by reaction with the acid with salt formation and at least one salt formed from the acid and the gas-forming component, the surface of the crystals of the one or more acids which are present in a bed being wet with water or with the solution of a component intended for the effervescent system and being at least partially reacted and being at most partially dried, and a further component present in finely divided form then being anchored on the surface and—optionally after partial reaction—the material being dried, wherein another acid and then at least a part of the gas-forming component are anchored to the surface of the wet acid crystals.

18. A process as claimed in claim 17, wherein dimethicone is combined with the effervescent system.

19. An effervescent tablet as claimed in claim 1, wherein said salts are acidic salts.

20. An effervescent tablet as claimed in claim 19, wherein 10–20% by weight of the total amount of the acids and gas forming components are said acidic salts.

21. An effervescent tablet as claimed in claim 3, wherein the substance is ambroxol, ranitidine or cimetidine and any anhydrous gas-forming component forms the outermost layer of the carrier crystal.

22. An effervescent tablet as claimed in claim 5, wherein the neutral excipient or carrier is selected from the group consisting of manitol, sorbitol, lactose, maltodextran and silica.

23. An effervescent tablet as claimed in claim 7, which contains citric acid and malic acid in a ratio of 20:1 to 3:1.

24. An effervescent tablet as claimed in claim 23, in which the ratio is 12:1 to 8:1.

25. An effervescent tablet as claimed in claim 8, wherein the gas-forming components are present in an amount which forms only the monosalt.

26. An effervescent tablet as claimed in claim 9, wherein 10–15% by weight of the total amount of gas-forming components have reacted to give the monosalt and are present in this form in a second or third layer.

27. An effervescent tablet as claimed in claim 10, wherein the at least one subsequent acid or salt is monosodium citrate and is diffused in the crystal lattice of the carrier particle.

28. An effervescent tablet as claimed in claim 13, in which the first layer is covered with at least two of said acids or alkali metal salts thereof.

29. An effervescent tablet as claimed in claim 15, in which the alkali-sensitive substance is acetylcystine, captopril or monoxidil and wherein the layer applied to the carrier crystals is covered with the gas-forming components by means of citric acid or fumaric acid.

30. An effervescent tablet as claimed in claim 16, which contains at least 100 parts by weight of sucralfate or paracetamol incorporated in the layer containing the gas-forming components and the carrier crystals are present as a mixture with anhydrous sodium carbonate.

* * * * *